United States Patent
Whalen, III et al.

(10) Patent No.: US 8,195,266 B2
(45) Date of Patent: Jun. 5, 2012

(54) MICROELECTRODE SYSTEMS FOR NEURO-STIMULATION AND NEURO-SENSING AND MICROCHIP PACKAGING AND RELATED METHODS

(75) Inventors: John J. Whalen, III, Davie, FL (US); James D. Weiland, Valencia, CA (US); Mark S. Humayun, Glendale, CA (US)

(73) Assignee: Doheny Eye Institute, Los Angeles, CA (US)

( * ) Notice: Subject to any disclaimer, the term of this patent is extended or adjusted under 35 U.S.C. 154(b) by 941 days.

(21) Appl. No.: 11/540,087

(22) Filed: Sep. 29, 2006

(65) Prior Publication Data
US 2007/0123766 A1    May 31, 2007

Related U.S. Application Data
(60) Provisional application No. 60/722,312, filed on Sep. 29, 2005.

(51) Int. Cl.
*A61B 5/04* (2006.01)
*A61N 1/05* (2006.01)
(52) U.S. Cl. ........ 600/373; 600/377; 600/378; 600/393; 600/395; 607/116; 607/119; 607/137
(58) Field of Classification Search .................. 600/373, 600/377–379, 393, 395; 607/116, 119, 137
See application file for complete search history.

(56) References Cited

U.S. PATENT DOCUMENTS
| | | | |
|---|---|---|---|
| 3,207,680 A | 9/1965 | MacNamara | |
| 4,969,468 A | 11/1990 | Byers et al. | |
| 5,234,594 A | 8/1993 | Tonucci et al. | |
| 5,264,722 A | 11/1993 | Tonucci et al. | |
| 7,190,049 B2 * | 3/2007 | Tuominen et al. | 257/618 |
| 7,267,859 B1 * | 9/2007 | Rabin et al. | 428/131 |
| 7,465,661 B2 * | 12/2008 | Merritt et al. | 438/667 |

(Continued)

FOREIGN PATENT DOCUMENTS
WO    WO 00/09008 A1    2/2000
(Continued)

OTHER PUBLICATIONS
Chow, et al., "The subretinal microphotodiode array retinal prosthesis," *Ophthalmic Res.*, 30:195-198 (1998).
(Continued)

*Primary Examiner* — Lee Cohen
(74) *Attorney, Agent, or Firm* — G. Matthew McCloskey; McDermott Will & Emery LLP

(57) ABSTRACT

Microelectrode assemblies and related methods are disclosed for bio-stimulating and/or bio-sensing a target tissue. The assemblies can include a two-side substrate, an array of microelectrodes, each of the microelectrodes including a nano-wire embedded within the substrate and extending from a proximal end to a distal end and through the substrate, each nano-wire having a diameter preferably less than 1 μm. The substrate can include portions made of nano-porous material (s) through which the microelectrodes pass. The substrate with the embedded nano-wires can effectively be fluid impermeable. The proximal ends of the nano-wires can be adapted to be connected to an electronic device and the distal ends are adapted to be disposed in a biological environment for bio-stimulating a target tissue and/or bio-sensing activities of the target tissue. Suitable alloys such as platinum, platinum-iridium, and/or other noble-metal-alloyed compositions can be used for the nano-wires.

6 Claims, 10 Drawing Sheets

U.S. PATENT DOCUMENTS

2002/0158342 A1    10/2002    Tuominen et al.

FOREIGN PATENT DOCUMENTS

| WO | WO 01/70873 A2 | 9/2001 |
|---|---|---|
| WO | WO 03/046265 | 6/2003 |
| WO | WO 2004/097894 | 11/2004 |

OTHER PUBLICATIONS

De Juan, et al., "Histopathology of experimental retinal neovascularization," *Invest. Ophthamol.*, 30:1495-1503 (1989).

Eckmiller, et al., "Learning retina implants with epiretinal contacts," *Ophthalmic Res.*, 29:281-28 (1997).

Grumet, et al., "In-vitro electrical stimulation of human retinal ganglion cell axons," ARVO abstracts, Ft. Lauderdale, FL, p. 50 (2000).

Grumet, et al., "Ten Micron Diameter Electrodes Directly Stimulate Rabbit Retinal Ganglion Cell Axons," ARVO abstracts, Ft. Lauderdale, FL, p. 3883 (1999).

Humayun, et al. "Bipolar surface electrical stimulation of the vertebrate retina," *Arch. Ophthalmol.*, 112:110-116 (1994).

Humayun, et al., "Pattern electrical stimulation of the human retina," *Vision Res.*, 39:2569-2576 (1999).

Majji, et al., "Long term histological and electrophysiological results of an inactive epiretinal electrode array implantation in dog," *Invest. Ophthalmol. Vis Sci.*, 40:2073-2081 (1999).

Scribner, et al., "Infrared focal plane array technology," *Proc. IEEE*, 79:66-85 (1991).

Shyu, et al., "Electrical Stimulation in Isolated Rabbit Retina," *IEEE*, 14:290-298(2000).

Tonucci, et al., "Nanochannel array glass," *Science*, 258: 783-785 (1992).

Veraart, et al., "Visual sensations produced by optic nerve stimulation using an implanted self-sizing spiral cuff electrode," *Brain Res.*, 813: 181-186 (1998).

West, et al., "Strength-duration characteristics of myelinated and non-myelinated bulbospinal axons in the cat spinal cord," *J. Physiol.* (London), 337: 37-50 (1983).

Wyatt, et al., "Ocular implants for the blind," *IEEE Spectrum*, 112: 47-53 (1996).

Yagi, et al., "Implantation of the artificial retina," *Nippon Rinsho*, 57: 1208-1215 (1999).

Zrenner, et al. "Can subretinal microphotodiodes successfully replace degenerated photoreceptors?" *Vision Res.*, 39: 2555-2567 (1999).

Scribner, et al., "Intraocular Retinal Porsthesis Test Drive", 2001 Proceedings of the 23d Annual EMBS International Conference, Oct. 25-28, 2001, Istanbul, Turkey, vol. 1 of 4, Conference 23, pp. 3430-3435.

Rabin, et al., "Formation of Thick Porous Anodic Alumina Films and Nanowire Arrays on Silicon Wafers and Glass", Aug. 2003, Advanced Function Materials, Wiley VCH, Wienheim, pp. 631-638.

Bauer, et al., Biological Applications of High Aspect Ratio Nanoparticles, J. Mater. Chem., vol. 14, Jan. 14, 2004, pp. 517-526.

Humayun, et al., "Towards a Completely Implantable, light-Sensitive Intraocular Retinal Prosthesis", Proceedings of the 23d Annual EMBS International Conference, Oct. 25-28, 2001, Istanbul, Turkey, pp. 3422-3425.

Baumgärtner, et al., "The Electrodeposition of Platinum and Platinum Alloys", Platinum Metals Rev., vol. 32, No. 4, 1988 pp. 188-197.

Whalen, et al., "Electrochemical Deposition of Platinum from Aqueous Ammonium Hexachloroplatinate Solution", J. Electrochemical Society, vol. 152, No. 11, Sep. 21, 2005, pp. C738-C743.

International Search Report for corresponding PCT Application No. PCT/US2006/038061, 7 pp, (Sep. 2007).

Written Opinion for corresponding PCT Application No. PCT/US2006/038061, 18 pp, (Sep. 2007).

* cited by examiner

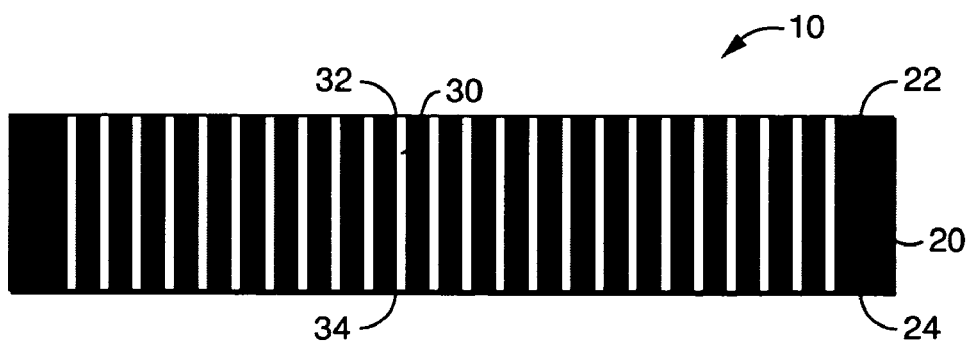
FIG. 1
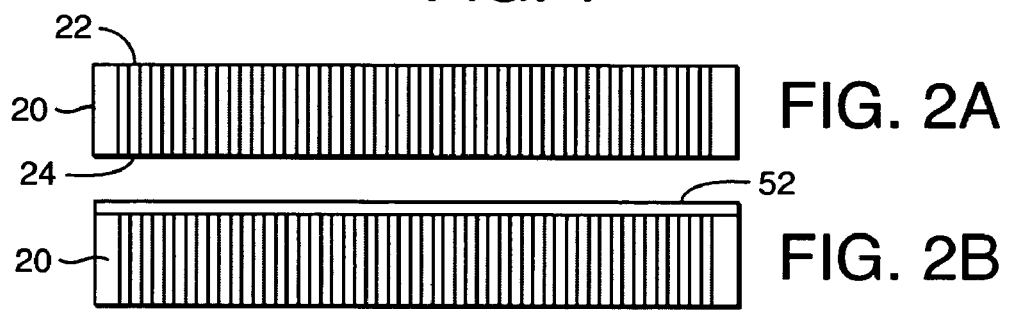
FIG. 2A
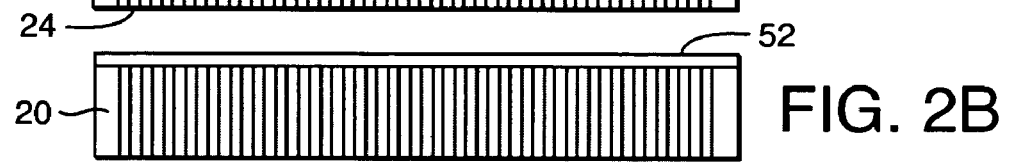
FIG. 2B
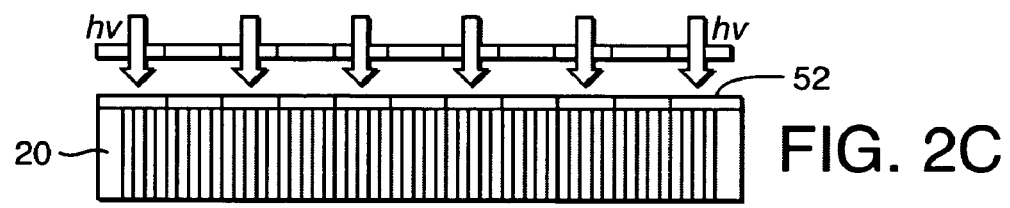
FIG. 2C
FIG. 2D
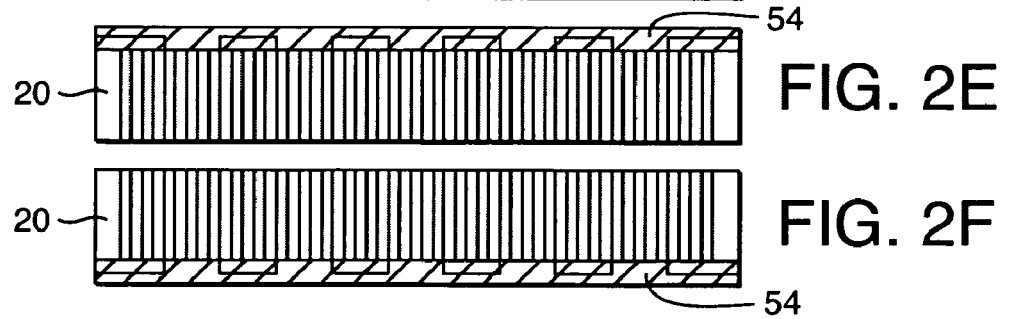
FIG. 2E
FIG. 2F
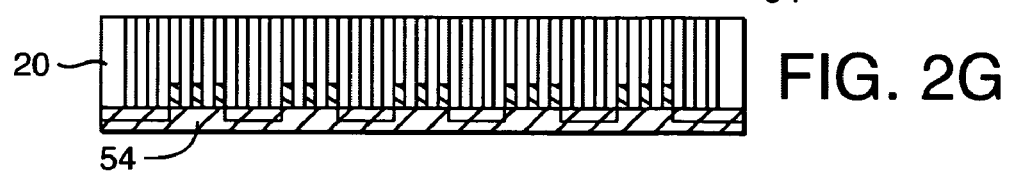
FIG. 2G
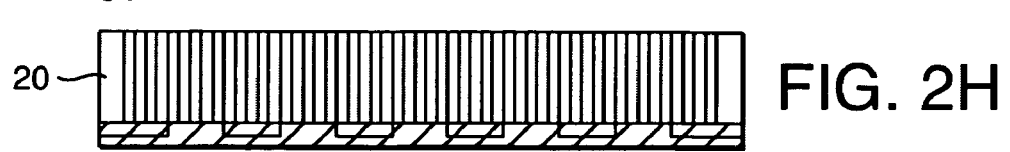
FIG. 2H

MICROELECTRODE SYSTEMS FOR NEURO-STIMULATION AND NEURO-SENSING AND MICROCHIP PACKAGING AND RELATED METHODS

RELATED APPLICATION

The present application claims the benefit of U.S. Provisional Application No. 60/722,312 filed on 29 Sep. 2005, the contents of which are incorporated in their entirety herein by reference.

TECHNICAL FIELD

The present disclosure relates to microelectrode systems for in vivo and/or in vitro neuro-stimulation and neuro-sensing and microchip packaging, and methods of making the microelectrode systems. More particularly, the present disclosure relates to nano-scale microelectrode systems and methods of making the nano-scale microelectrode systems.

BACKGROUND

A microelectrode system used in neuro-stimulation and neuro-sensing typically includes an array of microelectrodes used as signal sources or a sensor interface for generating or receiving electrical signals, thereby to stimulate or sense activities in tissues.

The microelectrodes in a neuro-stimulation or sensing device are typically connected to an electronic device, for example, a microchip, by interconnects. The electronic device is preferably be protected in a fluid impermeable package and the interconnects are the only part of the device that penetrate through the fluid impermeable package. In the development of a microelectrode array embedded in a substrate, the substrate/electrode structure preferably resists fluid penetration so as to ensure the electronic device is not damaged by short circuiting or corrosion. Fluid penetration through the electrode or substrate structure can occur in one of the following ways: 1) through the electrode itself, 2) through the substrate, or 3) along the interface between the electrode and substrate. Appropriate material selection for the electrode and the substrate and appropriate manufacturing process are needed to produce a fluid impermeable microelectrode system.

One conventional microelectrode system includes an array of microelectrodes patterned on a top side of a two-dimensional, rigid substrate (e.g. silicon wafer). This approach is capable of producing small microelectrodes; however, the total number and size of the microelectrodes are limited by the need to pattern electrical leads, which are on the same side of the substrate, for each electrode. As a result, wide channels need to be constructed on the substrate to accommodate the individual electrical lead for each electrode. Thus the number of the electrodes in a unit area is limited.

In some instances, such as retinal prosthesis applications, the target tissue is curved, and the microelectrode array should preferably conform to the target tissue structure to avoid damage to the tissue. The prior art microelectrode arrays generally fail to conform to a target tissue.

Therefore, there is need for an improved microelectrode system that overcomes one or more of the problems set forth above.

SUMMARY

Embodiments of the present disclosure provides a microelectrode assembly used for neuro-stimulating and neuro-sensing devices and microchip packaging, and methods of making the microelectrode assembly. In one aspect, the microelectrode assembly for bio-stimulating and/or bio-sensing a target tissue includes a substrate having a first side and a second side, an array of microelectrodes, each of the microelectrodes including a nano-wire embedded within the substrate and extending from a proximal end at the first side to a distal end at the second side, each nano-wire having a diameter less than 1 µm. The substrate with the embedded nano-wires can be fluid impermeable, or essentially so. The proximal ends of the nano-wires are adapted to be connected to an electronic device and the distal ends are adapted to be disposed in a biological environment for bio-stimulating a target tissue and/or bio-sensing activities of the target tissue. In one embodiment, the substrate can be made from aluminum oxide and the nano-wires from platinum and/or a suitable platinum-iridium alloy.

In another aspect, a method of making a microelectrode assembly having an array of microelectrodes for bio-stimulating and/or bio-sensing a target tissue includes providing a substrate having a first side and a second side and an array of nano-channels passing through the substrate from the first side to the second side, each of the nano-channels having a diameter less than 1 µm, depositing a layer of electrically conductive material on the first side, and electrodepositing an electrically conductive material into the array of nano-channels to fill the nano-channels from the second side to form the array of microelectrodes. In one embodiment, the substrate is made from aluminum oxide and the electrically conductive material for depositing into the nano-channels is platinum and/or a suitable platinum-iridium alloy.

According to a further aspect of the present disclosure, an electronic system includes an electronic device and a fluid impermeable packaging system for packaging the electronic device. The fluid impermeable packaging system includes a microelectrode assembly as described above.

According to yet another aspect of the present disclosure, a method of making a microelectrode assembly having an array of microelectrodes for bio-stimulating and/or bio-sensing a target tissue includes providing a substrate having a first side and a second side and an array of nano-channels passing through the substrate from the first side to the second side, the substrate having a barrier layer disposed over the first side, each of the nano-channels having a diameter less than 1 µm, patterning the barrier layer to define a pattern for the array of microelectrodes, depositing a layer of electrically conductive material on the first side, and electrodepositing an electrically conductive material into the array of nano-channels to fill the nano-channels from the second side to form the array of microelectrodes.

BRIEF DESCRIPTION OF THE DRAWINGS

Aspects of the disclosure may be more fully understood from the following description when read together with the accompanying drawings, which are to be regarded as illustrative in nature, and not as limiting. The drawings are not necessarily to scale, emphasis instead being placed on the principles of the disclosure. In the drawings:

FIG. 1 is a schematic cross-sectional view of an embodiment of a microelectrode assembly according to the present disclosure;

FIG. 2 schematically shows a process of making the microelectrode assembly of FIG. 1;

Figure 3:
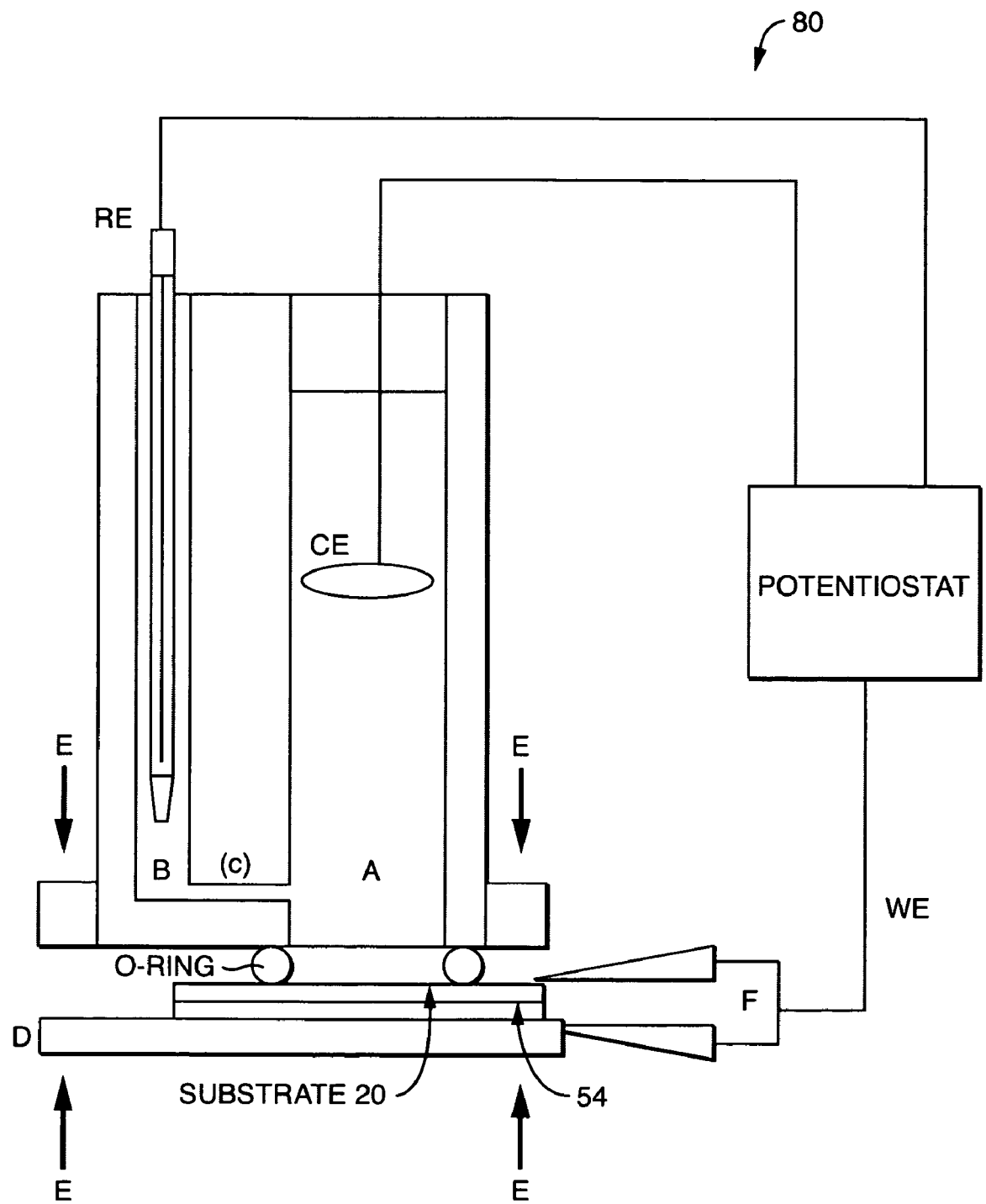
FIG. 3 is a schematic view of an electrodeposition system for making the microelectrode assembly of FIG. 1.

It should be understood by one skilled in the art that the embodiments depicted in the drawings are illustrative and variations of those shown as well as other embodiments described herein may be envisioned and practiced within the scope of the disclosure.

DETAILED DESCRIPTION

The present disclosure provides a microelectrode assembly used for neuro-stimulating and neuro-sensing devices and microchip packaging, and methods of making the microelectrode assembly.

FIG. 1 illustrates a cross-sectional view of one embodiment of the microelectrode assembly. As shown in FIG. 1, the microelectrode assembly 10 includes a substrate 20, which includes a first side 22 and a second side 24, and an array of nano-wires 30 individually extending from a proximal end 32 at the first side 22 to a distal end 34 at the second side 24. The proximal ends 32 and the distal ends 34 may be disposed in the plane of the surfaces of the substrate 20 as shown in FIG. 1. Alternatively, the proximal ends 32 and the distal ends 34 may extend above or below the surfaces of the substrate 20. In one embodiment, the substrate 20 is made from a ceramic material, for example, aluminum oxide (crystalline aluminum oxide or polycrystalline aluminum oxide). In another embodiment, the substrate 20 is made from a flexible material, for example, polymer. The nano-wires 30 are made from an electrically conductive material, preferably platinum. The nano-wire 30 has a rod-like or wire-like shape with a cross-sectional diameter from a few nanometers to about one micrometer.

In one embodiment, the aluminum oxide substrate 20 is about 60 μm thick and the diameter of the nano-wires 30 is about 50 nm. The size, spacing, and pattern of the nano-wires 30 can be different in different embodiments and can be controlled in the manufacturing process, which will be described in detail below. The substrate 20 with the embedded nano-wires 30 is fluid impermeable. The proximal ends 32 of the nano-wires 30 are adapted to be connected to an electronic device and the distal ends are adapted to be disposed in a biological environment for bio-stimulating a target tissue or bio-sensing activities of the target tissue. The microelectrode assembly 10 can be reversed, where the distal ends 34 are connected to the electronic device and the proximal ends 32 are disposed in the biological environment (e.g., in vivo or in vitro).

FIG. 2 schematically illustrates a process of making the microelectrode assembly 10 according to the present disclosure. A nano-channeled aluminum oxide substrate 20, which can be obtained in the market, is first provided as shown in step (a). In one embodiment, each nano-channel has a cross-sectional diameter from a few nanometers to about one micrometer. The nano-channeled substrate 20 is spin-coated with photoresist 52 on one side of the substrate (for example, the first side 22 as shown in FIG. 2) in step (b). A contact lithography mask with a pattern matching the desired microelectrode array geometry is placed over the photoresist 52, and the photoresist 52 is exposed, through the mask, to a UV light source to polymerize the photoresist 52 in step (c). The patterned photoresist 52 is developed to remove unwanted, unpolymerized photoresist, leaving the substrate 20 with a patterned photoresist layer on the first side 22 in step (d). A layer of conductive material 54 (for example, a metal such as Au, Ag, Cu, etc.) is deposited by sputtering or evaporation over the top of the photoresist to seal the bases of the nano-channels that have not been sealed by the photoresist in step (e).

The substrate is placed with the conductive material layer 54 at the bottom of the substrate 20 onto an electrically conductive material plate, as shown in step (f) in FIG. 2 and in FIG. 3. An electrochemical cell is clamped over the openings of the nano-channels at the second side 24 of the substrate 20. In one embodiment, the cell is filled with aqueous ammonium hexachloroplatinate solution having a pH of approximately 7.4 to 7.8. In one embodiment, the solution composition is about 17 mM $(NH_4)_2PtCl_6$ and 150 mM $H_2NaPO_4$.

FIG. 3 schematically shows an electrodeposition system 80 used to electrodeposit platinum into the nano-channels to form the array of nano-wires 30. As shown in FIG. 3, the electrodeposition system 80 includes a three-electrode electrochemical system connected to a computer controlled potentiostat. The electrodeposition system 80 includes an electrochemical cell, which includes one larger diameter electrolyte column (A) and one smaller diameter electrolyte column (B), each connected to one another at the base via a cross-drilled Luggin capillary (C). The substrate is placed onto a copper plate (D), with the openings of the nano-channels facing up, and a polymer o-ring is placed on the top of the substrate 20. The column (A) is fixed over the o-ring using a steel spring-clamp (E). This provides a water-tight seal between the electrochemical cell and the substrate 20. The column (A) is filled with plating solution (the aqueous ammonium hexachloroplatinate solution). A toothless copper alligator clip (F) is used to make electrical contact between the working electrode lead (WE) and the conductive material layer 54 of the substrate 20. A platinum mesh counter electrode (CE) is suspended through the top opening of the larger column (A). A Ag/AgCl reference electrode (RE) is placed in the smaller-barreled column (B) of the cell. The cross-drilled Luggin capillary (C) allows for accurate potential measurement without disrupting the field between the working and counter electrodes. The reference electrode was tested vs. standard calomel electrode to confirm accuracy of measurements and consistency before the electrodeposition of platinum.

Figure 4A:
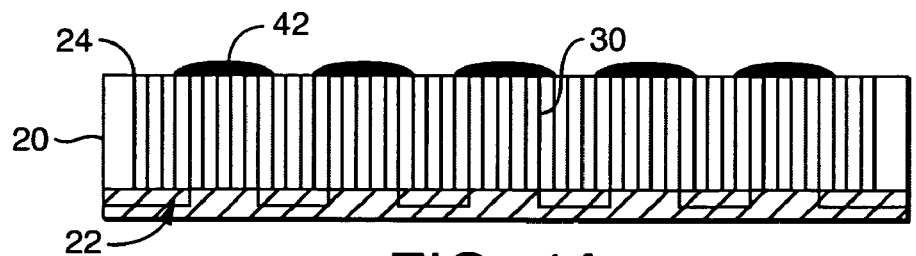
FIGS. 4A-4F schematically show cross-sectional views different embodiments of the microelectrode assembly according to the present disclosure.
Figure 4B:
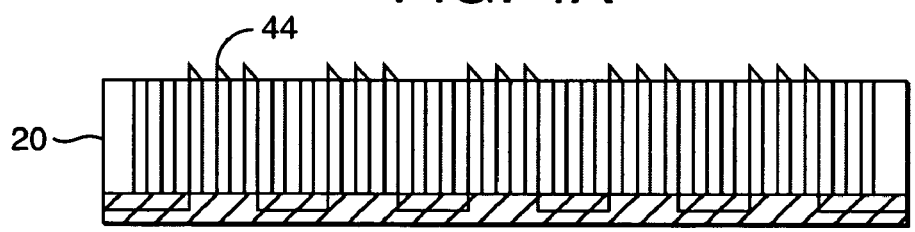
Figure 5:
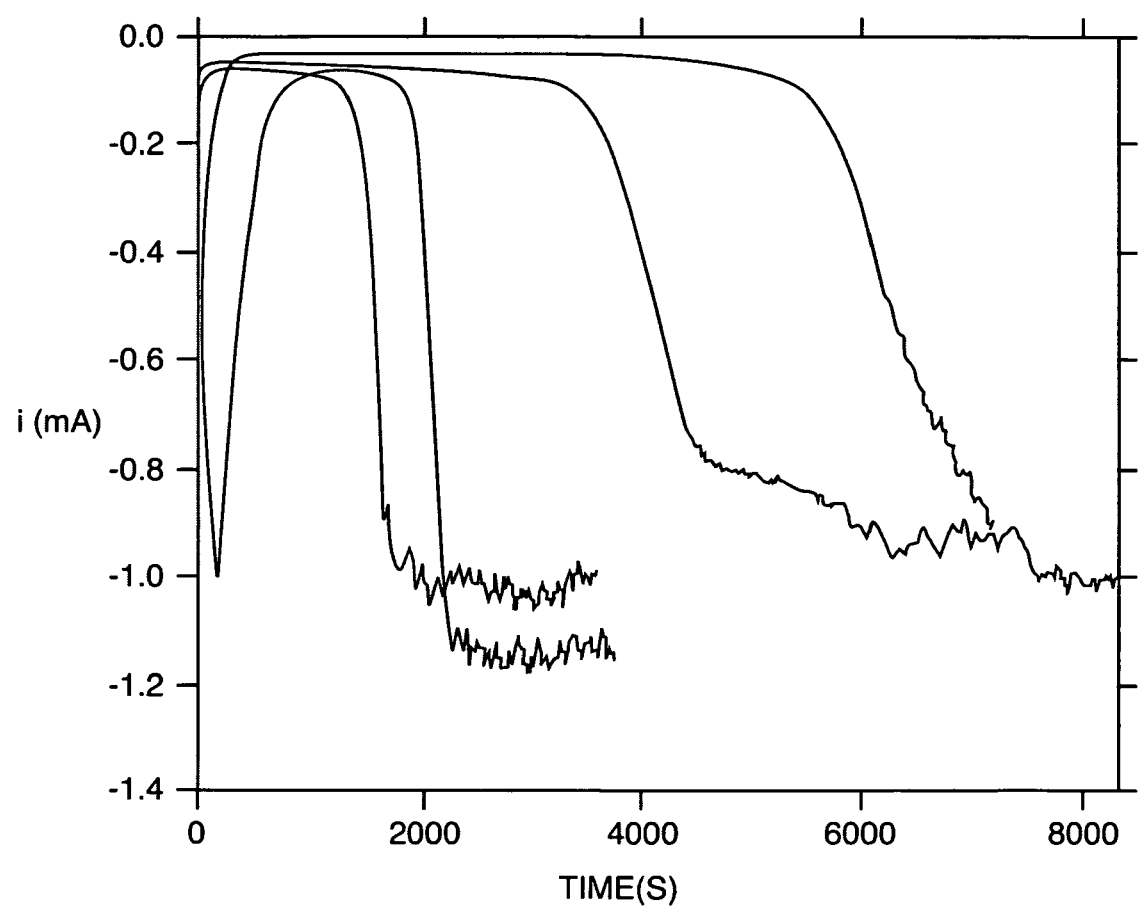
FIG. 5 shows a diagram of potentiostatic current vs. time transients in nano-wire electrodeposition.

According to one embodiment, under continuous stirring, platinum is potentiostatically deposited between −0.4 V to −0.6 V vs. Ag/AgCl, depending on the exact cell conditions. The electrolyte should be replaced after the efficiency of deposition is substantially decreased, for example, 50% platinum ions being consumed. In one example, platinum is deposited in 30 minutes intervals as shown in step (g) in FIG. 2. After completion of each 30 minutes interval, the electrolyte is replaced with fresh electrolyte solution and the procedure is repeated. Current vs. time plots can be collected for each potentiostatic deposition, and overlayed for comparison as shown in FIG. 5. A significant increase in current magnitude indicates that the platinum has filled through the substrate as shown in step (h) in FIG. 2, and the deposition is no longer geometrically confined by the nano-channels. At this point, in one embodiment, the deposition can be continued to form a continuous patch 42 of platinum over a few nano-wires as shown in FIG. 4A, or form a disc over each electrode, or, alternatively, the deposition can be terminated leaving an array of nano-scale protrusions 44 at each electrode site as shown in FIG. 4B, or leaving an array of nano-wires without extending above the top surface of the substrate 20.

Potentiodynamic deposition (deposition using non-steady-state control of the potential) can also be used. For example, a varying, non-steady-state potential, e.g., subject to cycling, cyclic potential stepping, and/or triangular-wave (ramp) cycling (within a maximum and minimum potential limit), can also be used to deposit metal. These cyclic or non-steady-state approaches deposit metal for a fixed portion of the cycle, then change the potential to allow byproducts of the deposition reaction to leave the active, deposition surface and provide time for new metal reactant to migrate to the deposition surface.

The substrate 20 with embedded nano-wires 30 are then mechanically polished by using a sharp blade or simply dragging across a polishing surface, or other mechanical polishing processes.

Figure 4C:
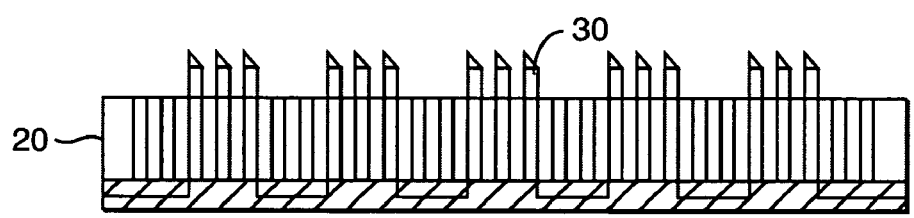
Figure 4D:
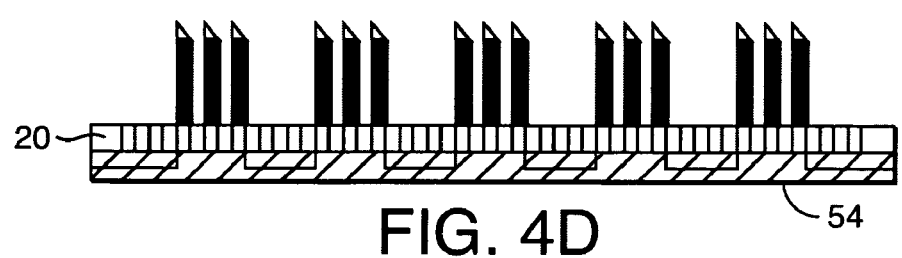

The second side 24 of the aluminum oxide substrate 20 can be etched to partially reveal the nano-wires 30 as shown in FIG. 4C and FIG. 4D. The etching can be performed in either basic or acidic solutions. Basic solutions include KOH and NaOH solutions. Concentrations can range from 50 mM to 5 M. Increasing the concentration causes more rapid and less controlled etching of the substrate 20. In the etching process, the substrate 20 may be mounted on a rotating stage or else stirring of the solution may be used to prevent accumulation of etching byproducts at the array surface, which might cause inhomogeneities.

Another method of etching the substrate 20 is by potential cycling or potential pulsing. The second side 24 of the substrate 20 is immersed in an aqueous solution and the potential on the nano-wires 30 can be set to the potential for hydrogen or hydroxyl plating. The potential can then be swept or stepped back to the open circuit potential. The resulting release of hydroxyl or hydrogen into the local solution etches the substrate 20. Impedance measurements can subsequently be performed to assess the change in the surface area of the nano-wires 30 revealed from the substrate 20.

Figure 6A:
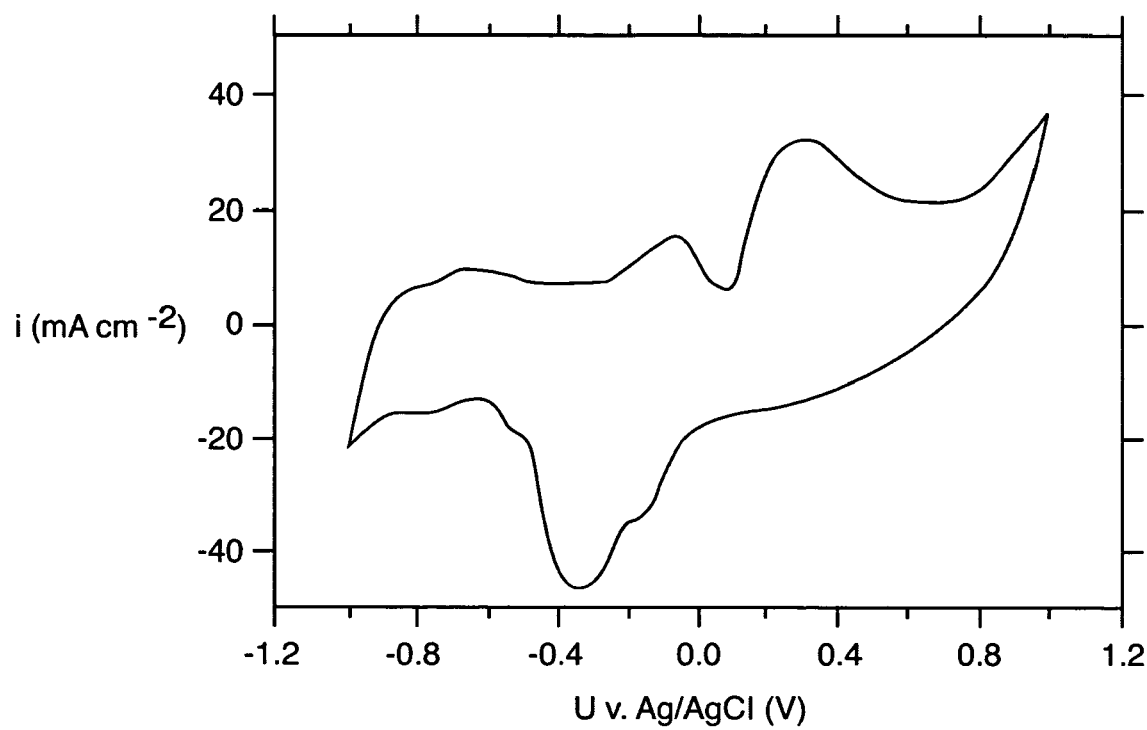
FIGS. 6A and 6B show diagrams of cyclic voltammetry data for platinum nano-wire electrode (6A) and platinum planar disk electrode (6B)
Figure 6B:
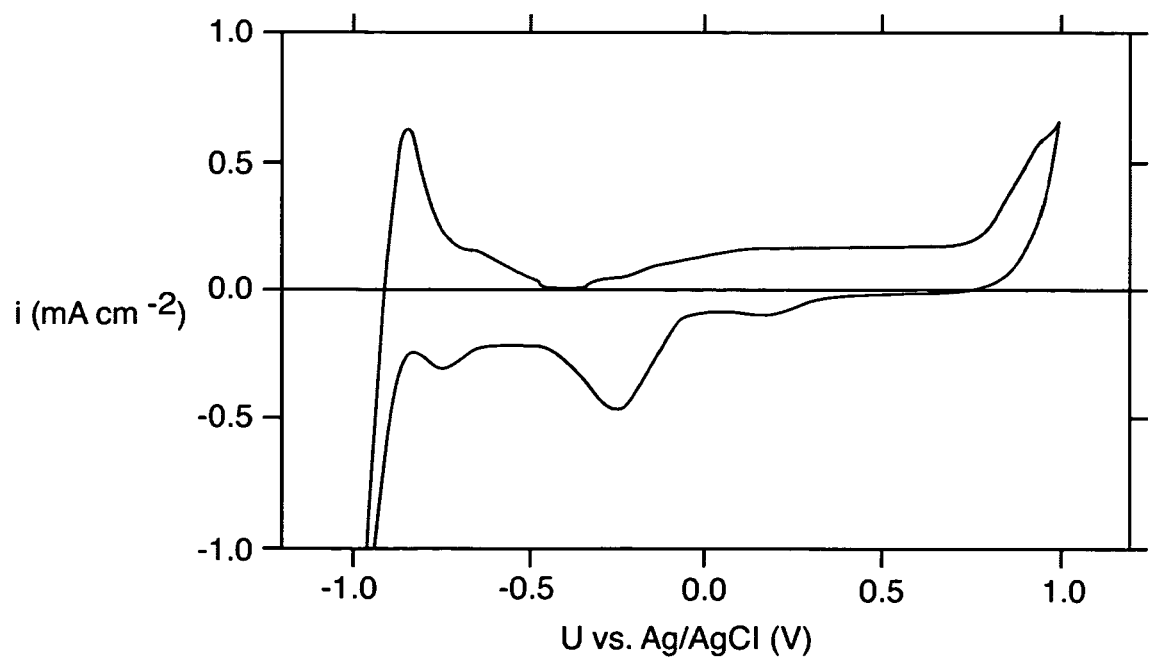

FIG. 6A and FIG. 6B show a comparison of cyclic voltammagrams for nano-wire electrode (FIG. 6A) and flat platinum disk electrode (FIG. 6B). Data has been normalized by the 2-dimensional surface area that the electrode occupies on the supporting substrate.

A cyclic voltammogram applies a potential (in volts) to the microelectrode surface and measures the resulting current response at the electrode-electrolyte interface. The voltage is swept, in a cyclic manner, over a range of potentials and the recorded data is plotted as a hysteresis loop of current vs. voltage (FIG. 6A and FIG. 6B). For the same applied potential, a microelectrode having a larger surface area will have a larger current response, because current scales with area (although the scaling may be non-linear).

In electrochemistry, normalizing the current by dividing it by the electrode surface area, i.e. current density (e.g., A cm$^{-2}$), is a commonly accepted practice for purposes of comparison of electrodes with different geometries, different compositions, etc. As such, two surface area terms have been defined in electrochemsitry: geometric surface area and real surface area. Geometric surface area refers to the two-dimensional, projected area which an electrode occupies. For example, the geometric surface area of a cone sitting on its base is a circle of radius, r (the base of the cone). The real surface area refers to the actual physical surface area of the electrode, accounting for surface roughness, i.e. contributions to surface area from the third-dimension.

In developing a neuro-stimulating array to fit within a confined spaced, the geometric area of each electrode will define the number of electrodes that can be placed inside a confined space. However, the current that can be delivered/injected (for some fixed potential, $U_{applied}$) by each electrode changes with real surface area (although the exact scaling is difficult to determine as it will be affected by the tortuosity of surface roughness features). For example, if two electrodes E1 and E2 of the same geometric surface area are tested, E2 having a larger real surface area than E1 (i.e. E2 has more surface roughness), to generate an equal amount of current from both electrodes, a larger potential need to be applied to E1 as compared to E2.

Referring to FIGS. 6A and 6B, the cyclic voltammograms in FIG. 6A and FIG. 6B plot the current density responses of a platinum nanowire microelectrode and a planar platinum disk electrode, in phosphate buffered saline (PBS) solution, recorded at a scan rate of 100 mV/s and scanned over the potential limits from −1.0 V to 1.0 V vs. Ag/AgCl reference electrode. For both plots, the current was divided by the geometric area of the electrode. Current was divided by real surface area to demonstrate that two microelectrodes occupying the same area on a microelectrode array grid are capable of generating significantly different current magnitudes for the same applied potential (i.e. driving force). The data shows that the nano-wire microelectrode can generate larger currents for the same applied potential. In other words, the nano-wire microelectrode is more efficient at injecting charge to the targeted tissue/cell.

Figure 4E:
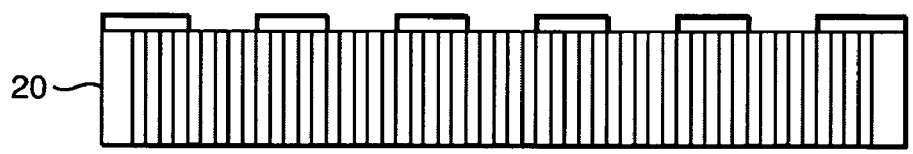
Figure 4F:
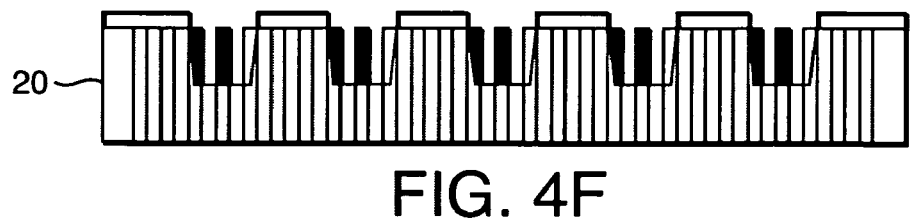

The evaporated/sputtered metal 54 may be etched away to reveal the base of the electrodes. FIG. 4E illustrates one embodiment, in which the metal layer 54 (shown in FIG. 4D) is removed by etching, leaving the patterned photoresist on the first side 22 of the substrate 20. The first side 22 of the substrate 20 may also be partially etched away to partially reveal the nano-wires 30 as shown in FIG. 4F.

Figure 7:
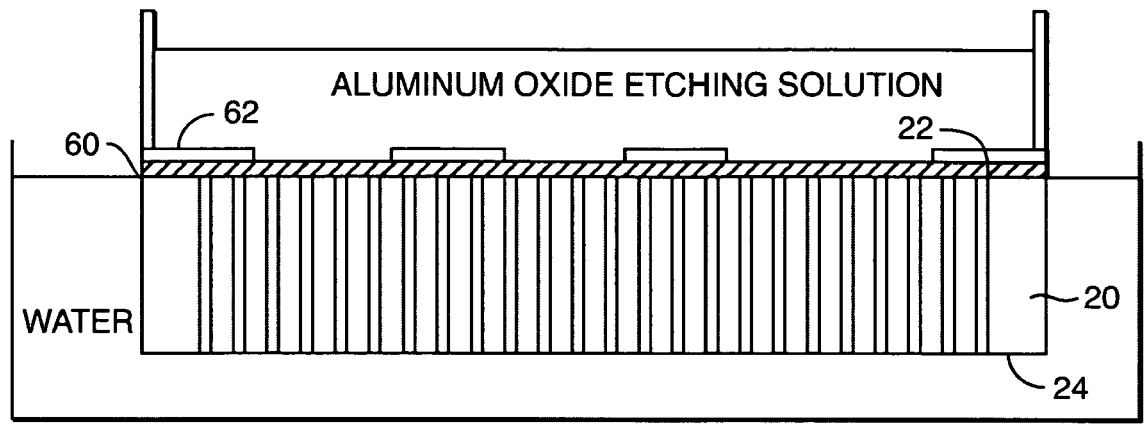
FIG. 7 is a schematic view of an assembly for making a microelectrode assembly using a substrate having a barrier layer according to one aspect of the present disclosure.

In the process of manufacturing nano-channeled aluminum oxide substrates, most of the nano-channeled aluminum oxide substrates are first manufactured with an aluminum oxide barrier layer at one side of the substrates. Typically, the barrier layer is removed before the nano-channeled aluminum oxide substrates enter the market. According to one aspect of the present disclosure, the microelectrode assembly may be manufactured with a nano-channeled aluminum oxide substrate that has an intact barrier layer 60 as shown in FIG. 7. The process of making the microelectrode assembly using the nano-channeled aluminum oxide substrate with the barrier layer is similar to the above described process. The barrier layer 60 is first patterned using a photolithography process. Photoresist 62 is first spin-coated onto the barrier layer 60. The photoresist 62 is then exposed to the UV light through a mask with a pattern and then developed, leaving the barrier layer exposed at areas where the microelectrodes will be. The substrate 20 can then be then clamped between two electrolyte chambers. The chamber facing the photoresist covered side of the substrate 20 is filled with aluminum oxide etching solution, while the chamber facing the nano-channeled side is filled with distilled water. The etchant only attacks the aluminum oxide barrier layer at areas not shielded by the photoresist 62. At those areas, the barrier layer is etched away until the nano-channels are exposed to the etchant. At this point, the distilled water held in the opposite chamber neutralizes the etchant, thus terminating the etching process before the nano-structure can be attacked.

After the barrier layer is patterned to expose the nano-channels, a layer of metal is evaporated/sputtered overtop of the photoresist side of the substrate, and the same electrodeposition process as described above using the substrate without the barrier layer can be used to electrodeposit the platinum into the nano-channels to form the nano-wires. Using the nano-channeled aluminum oxide substrates with the aluminum oxide barrier layer is economically advantageous because the process of removing the barrier layer is eliminated. Another advantage is that the aluminum oxide barrier layer improves the fluid impermeability of the substrate.

Nano-channeled aluminum oxide can be composed of randomly oriented nano-crystalline domains, separated by amorphous matrix. Amorphous regions may be more susceptible to dissolution, corrosion, and/or wear. Reducing amorphous matrix content can improve substrate integrity. One approach for increasing substrate crystallinity is through sintering. Suitable materials and/or methods may be used to increase crystal size, e.g., hot isostatic pressing (HIP)

The nano-channeled substrates (which are available in the market) may have a thickness equal to or greater than 50 μm and nano-channel diameters ranging from 5 nm to 200 nm. The array of the microelectrode assembly may include a single nano-wire or multiple nano-wires in the substrate, or one or more micro-scaled "patches" of nano-wires which are connected electrically in parallel at their bases. The dimensions of the nano-wires including the diameter of the nano-wire and the spacing between the nano-wires, the number of the nano-wires, and the dimensions of the substrate may be tailored to meet the requirements of a specific application.

In one embodiment, the electrodeposited platinum nano-wires comprise polycrystalline platinum and the substrate is polycrystalline aluminum oxide. From a fluid permeability perspective, those materials are highly resistant to water penetration. Susceptibility to fluid permeation is not only a function of the material type, but also of the material thickness. Nano-channeled aluminum oxide substrate has been fabricated with thicknesses greater than 50 μm, which is on the order required for packaging for electronics.

With the appropriate selection of materials for the electrodes and substrate, the only pathway for fluid permeation is along the interface between the electrodes and substrate. In general, the electrodeposition process used to create the nano-wires results in a complete filling of the channels in the substrate. For the case of platinum nano-wires, platinum complexes used for deposition, such as $[PtCl_6]^{2-}$, adsorb to the alumina surfaces thereby contributing to complete filling of the channels. Sintering may also be used to improve the integrity of the electrode/substrate interface.

Figure 8:
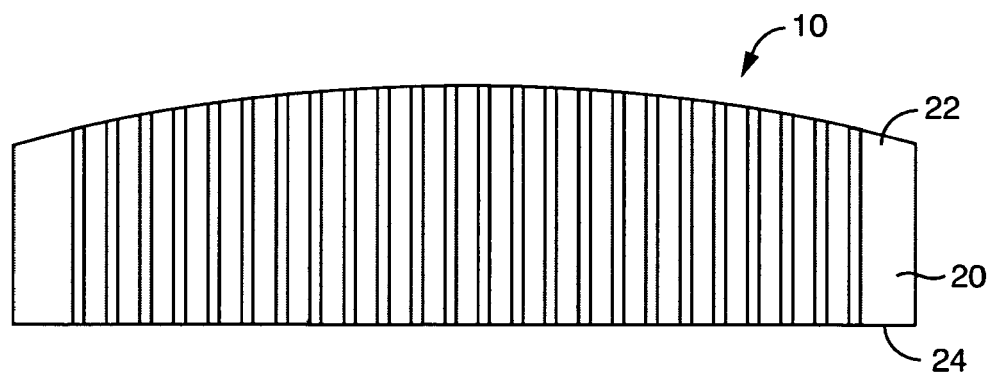
FIG. 8 is a schematic cross-sectional view of an embodiment of a microelectrode assembly according to the present disclosure.

In the situation that the microelectrode assembly is used in neuro-stimulating/neuro-sensing, the curvature of tissue, for example, the curvature of the retina may require that the microelectrode assembly be curved and conforms to the shape of the tissue. According to one aspect of the disclosure, the microelectrode assembly is fabricated with a relatively thick substrate and then is mechanically or chemical-mechanically polished to create a surface with a suitable radius of curvature as shown in FIG. 8.

An alternative approach to addressing the radius of curvature issue is to form the substrate in an aluminum film that has the desired radius of curvature on one side of the substrate. The pre-curved nano-channeled substrate with geometries conforming to the target tissue is subsequently filled with an electrically conductive material to form the nano-wires.

The end surface areas of the platinum microelectrodes revealed out of the substrate at one side of the substrate can be tailored. In one form, the nano-wires in the microelectrodes are flush with the surface of the substrate and hence have an exposed area that is related to the nano-wire diameter and the number of nano-wires in the substrate. The end surface area of the microelectrodes can be increased by partially etching the substrate to expose a given length of the nano-wires. The electrode surface area can be increased systematically by controlling the amount of substrate etching. According to another aspect, the morphology of electrodeposited platinum nano-wires is dependent on the deposition conditions, and under certain conditions the deposited platinum is highly porous. Thus the surface area of the microelectrodes can be increased by depositing highly porous platinum for the end-segments of the nano-wires.

Figure 9A:
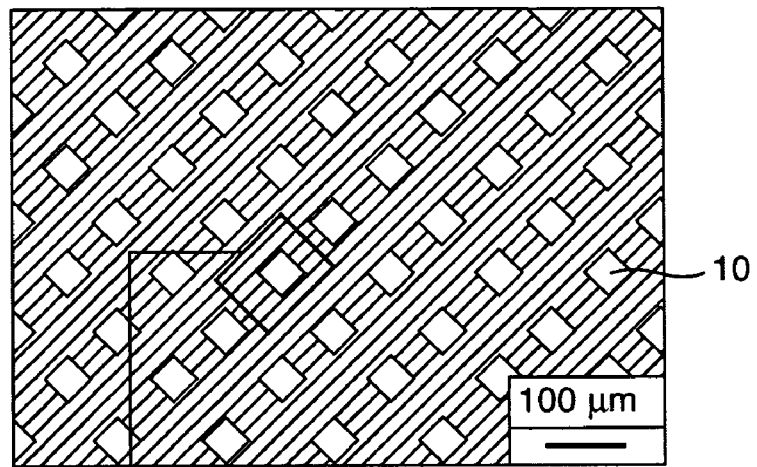
FIG. 9A illustrates a microelectrode system including multiple microelectrode assemblies each microelectrode assembly including an array of nano-wires.
Figure 9B:
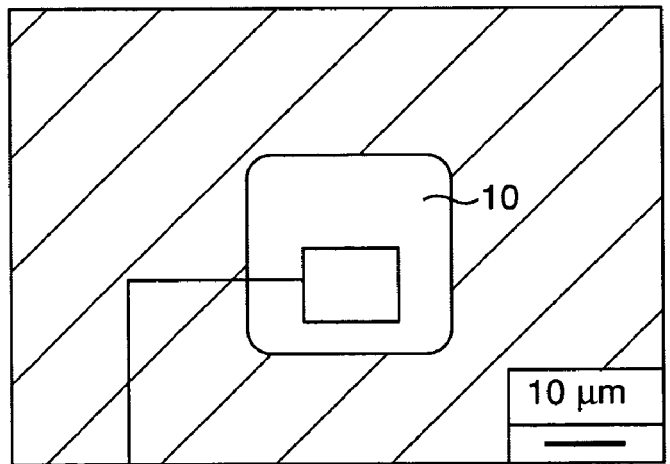
FIGS. 9B and 9C illustrate enlarged views of a microelectrode assembly of FIG. 9A.
Figure 9C:
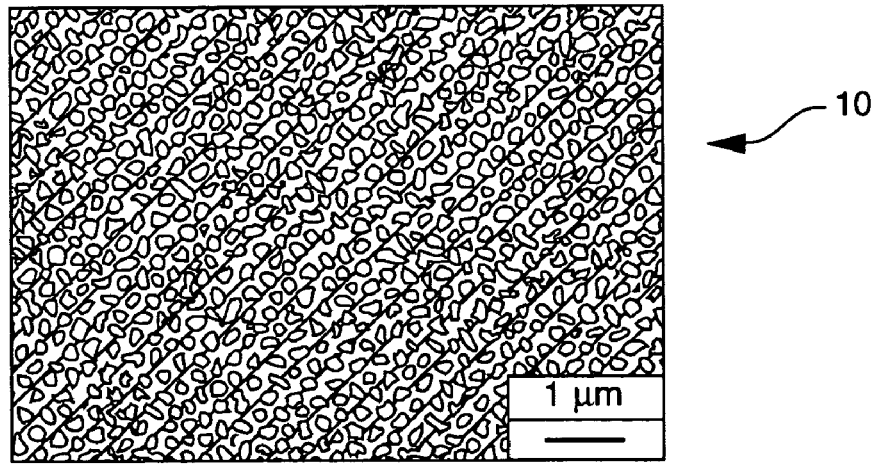

FIG. 9A illustrates a microelectrode system which includes multiple microelectrode assemblies 10 as described above. Each microelectrode assembly 10 is 50 μm×50 μm square with approximately 100 μm edge-to-edge spacing between two microelectrode assemblies 10 arranged in a square pattern. FIG. 9B shows an enlarged view of one microelectrode assembly 10 and FIG. 9C shows a further enlarged view of a part of the microelectrode assembly 10 to show the nano-wires.

Figure 10:
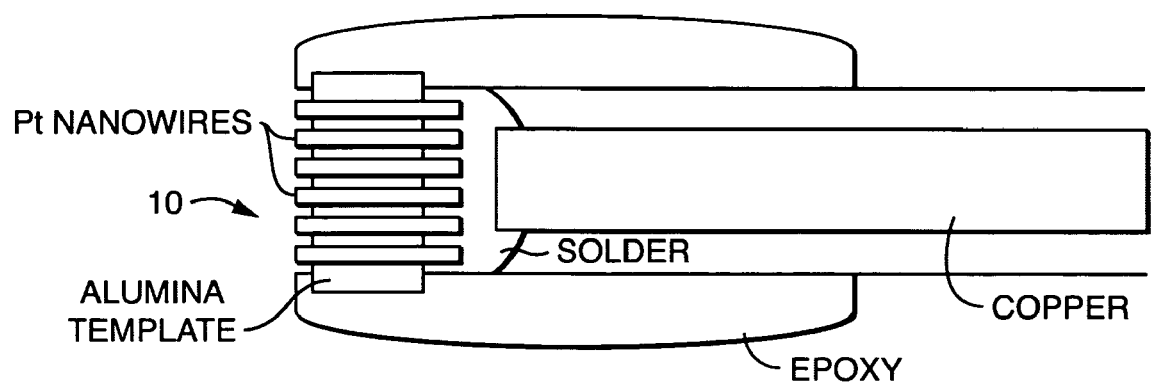
FIG. 10 shows a microelectrode probe including a microelectrode assembly.

FIG. 10 shows a microelectrode probe which includes a microelectrode assembly 10 connected to a copper wire by solder.

Figure 11:
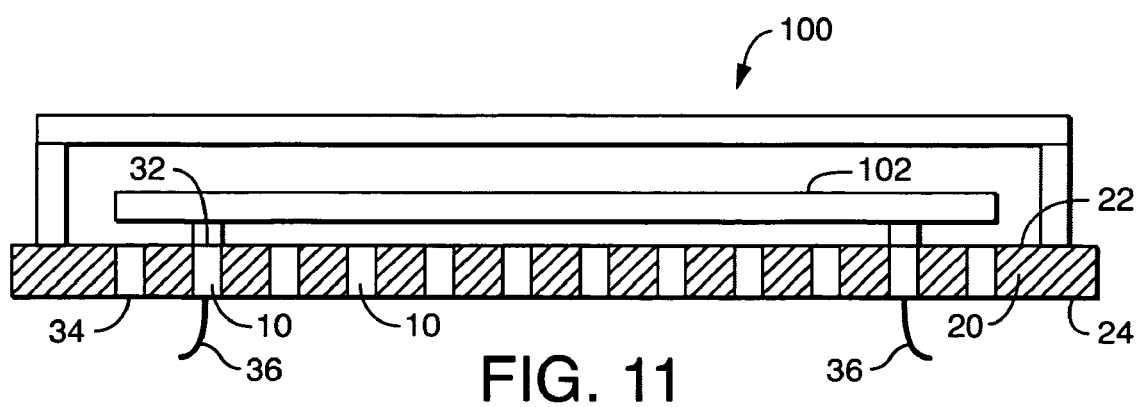
FIG. 11 is a schematic cross-sectional view of an embodiment of an electronic system having a microelectrode packaging system according to the present disclosure.

The microelectrode assembly may be used for packaging electronic devices. FIG. 11 illustrates an electronic system 100, which has an electronic device 102 (e.g., a microchip) packaged with a microelectrode system which includes multiple microelectrode assemblies 10 constructed according to the present disclosure. The proximal ends 32 of at least one microelectrode assembly 10 at the first side of the substrate 22 are connected to the electronic device 102 and the distal ends 34 at the second side of the substrate 24 connected to leads 36 or disposed in a biological environment for bio-stimulating a target tissue or bio-sensing activities of the target tissue. Because the nano-wires 30 penetrate through the supporting substrate 20, the leads can be constructed and patterned on the backside (i.e., the second side) of the substrate 20, thereby eliminating the problems associated with having electrodes, leads, and contacts on the same side of the packaging substrate.

The microelectrode assembly may be used in biomedical applications where electrical neuro-stimulation/sensing is implemented/required. This may include but is not limited to retinal prosthesis applications, cochlear implant applications, cardiac stimulation, cortical stimulation, and other possible implantable neurostimulatory or neurosensing device applications. The microelectrode assembly may also be used in research settings/applications, for example, measurement, mapping, stimulation, and sensing of neural activity or possibly chemical activity of cell cultures.

Preliminary helium leak tests using an ALCATEL™ ASM series helium leak test system were performed on circular nano-wire ceramic substrate pieces. Samples were positioned over a vacuum port connected to a mass spectrometer, calibrated for helium detection. Vacuum was applied on one side, while the opposite side of the substrate was exposed to helium gas. Spectrometer helium leak detection readings for three of the four samples were less than $10^{-11}$ ppm.

Nano-channeled aluminum oxide substrates are typically two-dimensional. Curved nano-channeled aluminum oxide substrates can be formed. Soft polymer substrate with nano-channels can also be used to form flexible arrays.

The nano-channeled aluminum oxide substrate can be substituted with other nano-porous substrate materials. Desirable criteria for the construction, design, or material selection for the substrate are that: 1) the nano-channels be continuous from one side of the substrate to the other, 2) the nano-channels are non-networking between one another, 3) the substrate is resistant to water permeation, and/or 4) the substrate is electrically insulating.

The diameter and length of the nano-channels can be varied. Channel diameter can vary from 1 nm to hundreds of nanometers. Channel length will be dependent on substrate thickness. The thickness should be on the order of micrometers (1-1000).

Platinum nano-wires can be substituted with other metals, metal alloy or metal oxide composition used for neural stimulation or neural sensing. This includes but is not limited to: platinum, platinum oxide, iridium, iridium oxide, platinum-iridium alloys, tantalum and tantalum oxide, carbon, rhodium and ruthenium.

The neural interface side at distal ends of the nano-wires of the microelectrode assembly can be tailored into different shapes. In one embodiment, the nano-wires comprising a single electrode are plated through the substrate and capped over to form a continuous patch of platinum over the top of each nano-wire. In another embodiment, the nano-wires are capped over and the caps are mechanically removed by polishing or milling to make each electrode an array of discrete nano-discs, coplanar with the substrate surface. In a further embodiment, the nano-wires are deposited so that the terminals are coplanar with the top surface of the nano-channeled substrate. In yet another embodiment, the substrate is partially etched to partially reveal the nano-wires. The surface area of the microelectrodes can be increased to a predefined surface area by controlling the etching procedure. According to another aspect of the disclosure, the surface features described above also can be used on the other side of the microelectrode assembly. For example, the metal layer 54 (in FIG. 4D) can be removed and the substrate can be partially etched to partially reveal the nano-wires. For another example, the metal layer 54 can be patterned to form metal patches connected to the nano-wires.

According to a further aspect of the present disclosure, a microelectrode assembly includes an array of electrodeposited platinum-iridium alloy nanowires penetrating through a two-dimensional, nano-channeled, aluminum oxide substrate, which can be used as a hermetic micro-electronic feedthrough device for biological and non-biological applications. Other noble-metal alloys may also be used for the nanowires, in accordance with the present disclosure. The structure of embodiments including such alloys can be similar to the structure as described above and shown in FIGS. 1-11.

In exemplary embodiments, platinum-Iridium (Pt–Ir) alloy nano-wires can be fabricated by electrodepositing from a solution comprised of ammonium hexachloroplatinate $(NH_4)_2PtCl_6$, sodium hydrogen phosphate $(Na_2HPO_4)$, and sodium hexachloroiridate $(Na_3IrCl_6)$. Electrodeposition involves the conversion of metal ions dissolved in solution into a deposit of metal atoms at an electrically conductive surface via electron transfer. This process is called electrochemical reduction. In one embodiment, platinum and iridium are simultaneously electrodeposited to form an alloy of platinum and iridium by electrodepositing from a mixed solution of ammonium hexachloroplatinate and hexachloroiridate. In another embodiment, oxide and/or hydrous oxides of either one or both metals (e.g., $Pt_xO_y$, $Pt_xOH_yIr_xO_y$, $Ir_xOH_y$) are simultaneously electrodeposited from the same mixed solution. It should be clear that other platinum-salt and iridium-salt solution chemistries commonly used for deposition of these two metals (in elemental, metal oxide, hydrous metal oxide, or alloy forms) can also be used for preparation of the deposited metal. Hexachloroiridate is only one example.

According to one aspect of the present disclosure, the platinum and iridium alloy nano-wires may be formed by the following exemplary process.

Electrolyte Preparation: two individual solutions (electrolytes) are first prepared. A separate platinum electrolyte solution and a separate iridium solution are prepared individually, and then mixed in different proportions to prepare different plating solution compositions. For platinum-iridium nano-wire deposition, the proportions of the two electrolytes can be varied to adjust the proportion of the two metals, i.e. platinum and iridium present in the alloy.

For one example, the iridium solution can be prepared by adding 0.195 g $Na_3IrCl_6$ in 15 mL 0.1M HCl. The result solution has an olive green color. The olive green solution is slightly boiled for about thirty minutes until a color change to a golden brown is observed. The solution is cooled to room temperature before preparing the Pt—Ir electrolyte. Skipping the cooling step may cause oxidation of iridium, which is indicated by a rapid change in the solution color from golden brown to an opaque, black color.

The platinum solution, for one example, can be prepared by mixing 0.350 g $(NH_4)_2PtCl_6$ and 1.75 g $Na_2HPO_4$ in 50 mL $H_2O$. This electrolyte requires no heating, only agitation via stirring or shaking. The solution has a yellow to orange transparent color with no visible precipitates. The stability of both electrolytes (iridium electrolyte and platinum electrolyte) is low, meaning that the solutions may undergo physical changes if left standing (unused) for prolonged periods. Further, these changes affect the ability to electrodeposit metal from these solutions in a negative manner. The platinum electrolyte is particularly unstable, and should therefore, be prepared close to the time of use. The platinum electrolyte shows a significant loss in plating efficiency (i.e., its ability to generate robust deposits) after 48-hours, and shows best performance if used within 12-hours of preparation.

The proportions of the platinum and iridium electrolytes can be varied to adjust the relative proportion of the two metals in the alloy. For nano-wire deposition, one of the factors controlling the composition of the solution is the pH of the resulting mixture. The ratio of platinum to iridium solution is set such that the pH of the mixed solution does not cause etching or dissolution of the nano-channeled aluminum oxide substrate. For example, pH of the final electrolyte used should not be lower than pH=3, and not higher than pH=11.

Nano-wire deposition: Nano-wire synthesis can be performed under potentiostatic (controlled voltage) control, to control nano-wire growth rate and composition. The procedure for nano-wire electrodeposition using platinum-iridium mixed solution is similar to the process described above for electrodepositing platinum only. Potentiodynamic deposition (deposition using non-steady-state control of the potential) can also be used. For example. Using potential cycling, cyclic potential stepping, and/or triangular-wave (ramp) cycling (within a maximum and minimum potential limit) can also be used to deposit metal. These cyclic approaches deposit metal for a fixed portion of the cycle, then change the potential to allow byproducts of the deposition reaction to leave the active, deposition surface and provide time for new metal reactant to migrate to the deposition surface.

Potentials for deposition are determined by comparing the cyclic voltammogram (cycled current-voltage sweeps) of the two pure electrolytes with that of the mixed platinum-iridium plating solution to identify the current ranges over which both platinum and iridium deposition are observed. The dependence of deposition rate on the applied voltage will be different for platinum and iridium, and therefore, the composition of the alloy can be controlled by varying two parameters: 1) the relative amount of platinum ions vs. iridium ions in the plating solution; 2) the potential used for metal deposition.

Figure 12:
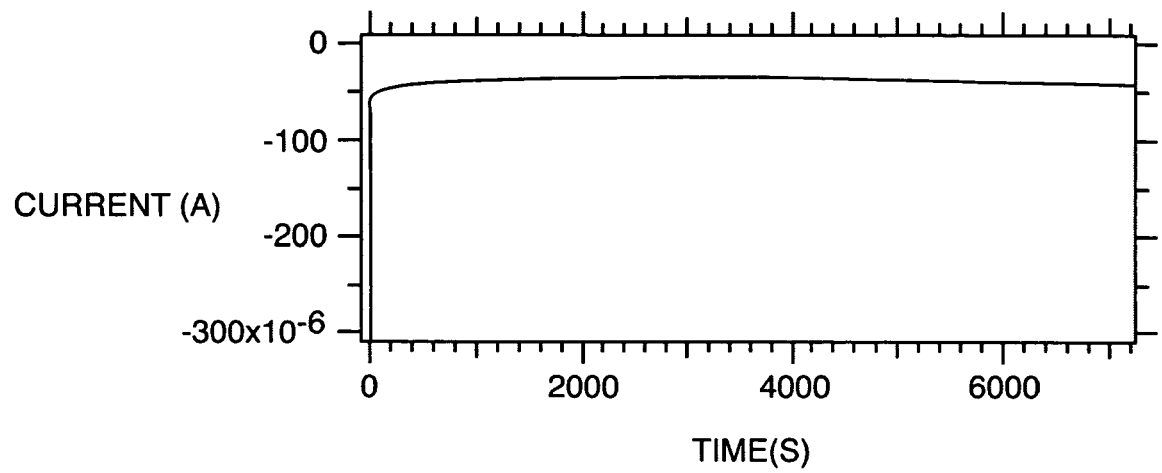
FIG. 12 shows a diagram of potentiostatic current vs. time transients in nano-wire electrodeposition according to one embodiment of the present disclosure.

In one embodiment, platinum-iridium alloy are electrodeposited into nano-channels within an aluminum oxide substrate under potentiostatic control at −0.5 V for 2 hrs from a solution comprised of 3:7 (Pt/Ir) solution. The current vs. time curve plots the measured current associated with nano-wire deposition as shown in FIG. 12. Nano-wires with approximately 10 micrometers in length were deposited. These nano-wires were isolated and filtered onto a nano-porous aluminum oxide filtration membrane, and a very preliminary assessment of composition was performed using X-ray Energy Dispersive Spectroscopy (EDS). The table below shows the percent compositions from the area tested (EDS also detected composition of the substrate below) in the left data column. The platinum and iridium compositions are separated from the other compounds detected and their fractional composition is calculated to be about 88% to about 12% by molar fraction, platinum to iridium.

Pt—Ir nano-wires have

| EDS Composition Analysis | | |
|---|---|---|
| Platinum | 44.0% | 88% |
| Iridium | 5.9% | 12% |
| Other Compounds | 50.1% | X | have improved nano-channel filling. Typically, deposition from electroplating solutions comprised of metal salts having low solubility results in deposited metals with porous surface structures. This is in comparison to solid, continuous, and dense deposits observed for metals deposited from solutions in which the metal salt has a greater solubility (like copper). Elevating temperature and introduction of convection (stirring) can improve deposit characteristics because both help to locally increase the concentration of ions, which are continuously being consumed by the electrodeposition process, near the microelectrode surface.

Because the plating solution contained both iridium chloride complexes and platinum chloride complexes, the total amount of metal ion in solution is greater than a solution of either of the single metal salts. Simultaneous co-deposition of the two metal ions increases the overall rate of metal deposition, which improves filling of the aluminum oxide nano-channels.

Pt—Ir alloys demonstrate improved mechanical properties over either of the pure metals. Alloying platinum with a small quantity of iridium (<10%) improves the mechanical properties of the deposits, providing elasticity (reversible deformation) while avoiding plasticity (irreversible deformation). For applications where exposing the nano-wires from the substrate, i.e., to increase the surface area contact with other electronics or for interfacing with biological tissue, etc., the Pt—Ir alloyed nano-wires are preferred because the mechanical properties of Pt—Ir alloyed nano-wires are enhanced over the properties of a nano-wire composed of only platinum or only iridium.

For electrical stimulation applications, Pt—Ir alloyed nano-wires demonstrate a large charge injection capacitance, and this improves stimulating efficiency. The charge injections properties of pure platinum and iridium/iridium oxide are well studied. Iridium/iridium oxide is capable of injecting larger quantities of charge to tissue than platinum, thus making it a more efficient charge injector. A stimulating electrode comprised of an alloy of platinum and iridium have a higher charge injection capacitance than a microelectrode of identical design, comprised only of platinum.

Figure 13:
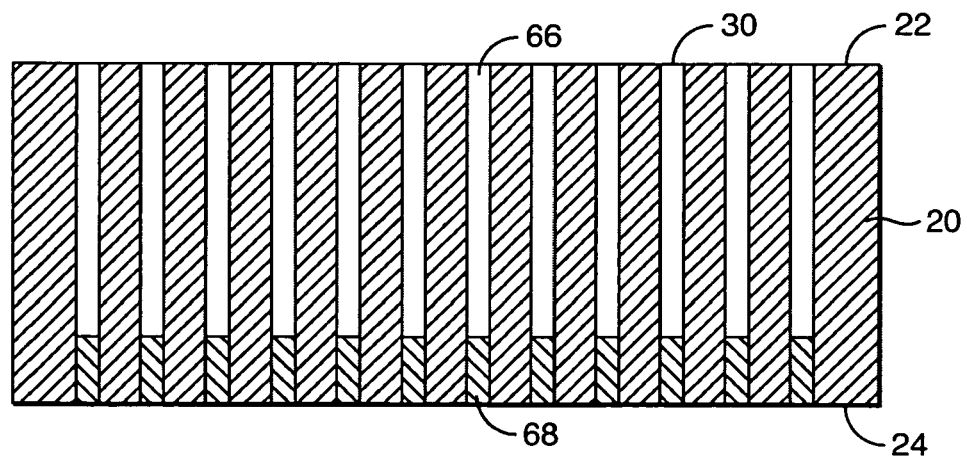
FIG. 13 shows a schematic cross-sectional view of an embodiment of a microelectrode assembly with each nano-wire including two sections according to one embodiment of the present disclosure and each section having a different elemental composition.

In a further embodiment, the nano-wires each includes at least two sections as shown in FIG. 13. A first section 66 is made from a first electrically conductive material and a second section 68 is made from a second electrically conductive material, which is different from the first electrically conductive material. The first section preferably is made from gold which possesses two advantages over platinum: 1) gold has a higher solubility in solution than platinum which will improve nano-channel filling and result in higher fluid impermeability; and 2) gold surface exposed to electrolyte can be coated with a chemically bonded, electrically insulating, Self-Assembled Monolayer (SAM) of alkane thiol (e.g., —S—$(CH_2)_x$—$CH_3$). The SAM forms a strong sulfide-gold (thiol) linkage to any exposed gold surface, which results in the alkane portion of the SAM forming a protective sheath over the gold. The second section preferably is made from a metal that is not susceptible to corrosion in vivo or in vitro.

In one embodiment, the first electrically conductive material is gold and the second electrically conductive material is platinum. In another embodiment, the second electrically conductive material is selected from a group consisting of platinum oxide, iridium, iridium oxide, platinum-iridium alloy, tantalum, tantalum oxide, carbon, and ruthenium. According to one aspect of the disclosure, the second section is intended to be used as an interface for bio-stimulation and/or bio-sensing and is disposed in a biological environment, because the second section is made from a material that is not susceptible to corrosion. The first section is used to connect to an electronic device or other devices. The first section is also resistant to hydrogen or hydroxide adsorption. Hydrogen and hydroxide adsorption to the second segment is used to etch away the template surrounding this segment, during the exposure process. By using a first segment which is resistant to hydrogen and hydroxide adsorption, the etching process is self-limited to the junction between the first and second segments. In the case where gold is used as the first segment, gold exposed to the external environment can be electrically isolated by treating with a non-conducting surface adhesion molecule (SAM), via a chemical linkage, for example: a thiol-linkage.

The process of electrodepositing the two electrically conductive materials (e.g. two metals) can be similar to the process of depositing one metal as described above. The first metal can be electrodeposited using a solution having ions of the first metal. For example, the electrolyte and the process of electrodepositing gold are known in the art. After the electrodeposition of the first metal reaches a predetermined level, the second metal is electrodeposited into the nano-channels using an electrolyte having ions of the second metal. In a similar fashion, the second metal (e.g. platinum) can be electrodeposited first to a predetermined level; and then, deposition of the first metal can be performed overtop, to complete filling of the nano-channels. The electrodeposition system and the polishing process can be the same as used in platinum electrodeposition. The microelectrode assembly also can have different surface features as described previous embodiments.

Gold can be electrodeposited using any number of commercial available gold plating solution compositions, or plating solution methods (e.g. compositions and methods developed by Technics Corp. or previously published). The only requirements are that the plating solution, and the plating process itself do not adversely affect the nano-channeled substrate nor can they adversely affect the final nano-wire: substrate structure or its function. For example, gold plating solutions which use lead-based additives (a common additive used in some plating solutions) would preferably not be used, to avoid incorporation of lead in the final structure whose function requires implantation into tissue. It is known that lead exposure is potentially cytotoxic. Electroless plating techniques may be used in the alternative or in addition to such electrodeposition techniques. In exemplary embodiments according to the present disclosure, a microelectrode assembly (e.g., one used for neuro-stimulating and neuro-sensing devices and microchip packaging) can include a substrate including portions that utilize nano-porous material(s) as opposed to relying on nano-channels. By having a network of interconnected pores of desired size (e.g., on the nano or sub-micron size), such nano-porous can allow increased substrate thickness and thus water-impermeability for devices according to the present disclosure. An example of such is depicted in FIG. 14.

Figure 14:
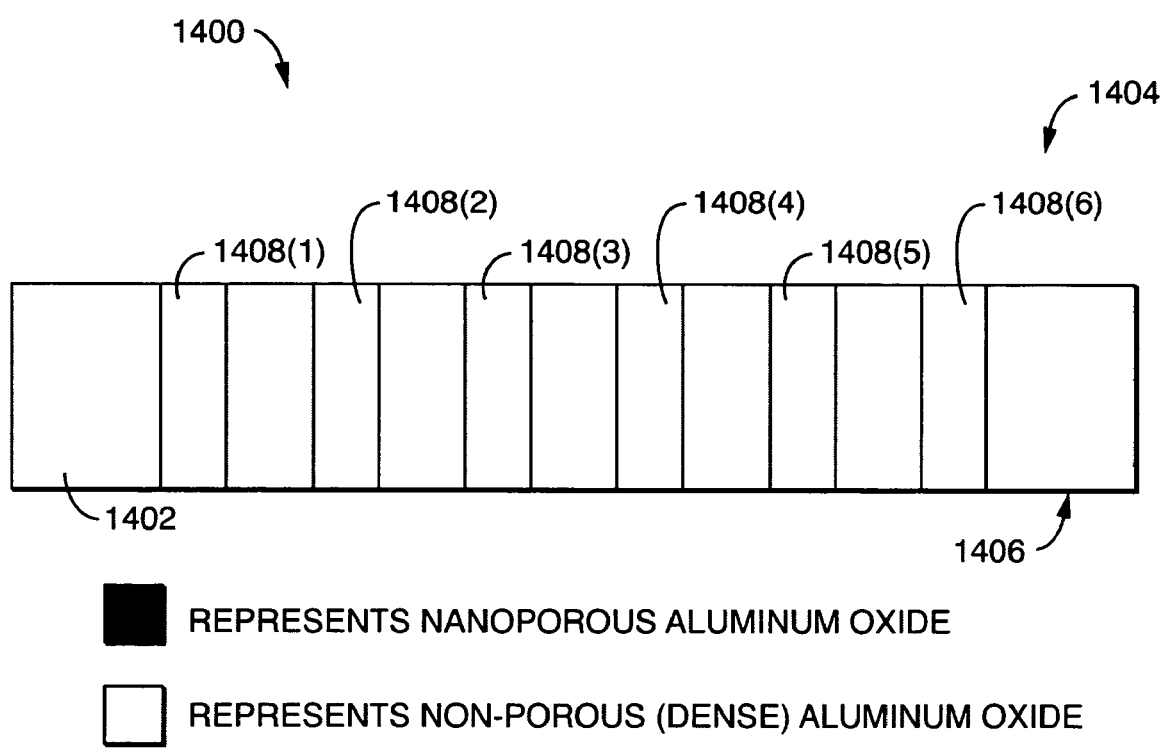
FIG. 14 is a schematic cross-sectional view of an embodiment of a substrate including nanoporous sections penetrating from one substrate side to the other separated by dense, non-porous sections of electrically-insulating material.

FIG. 14 is a schematic cross-sectional view of an embodiment 1400 of a substrate 1402 with first and second sides 1404 and 1406. The substrate includes nano-porous sections or portions 1408(1)-1408(6), having a desired cross-section, penetrating from one substrate side 1404 to the other 1406 and through which nano-wires (not shown) according to the present disclosure can be disposed. Substrate 1402 includes a suitable pattern that functions to provide a template or oriented structure (e.g., framework) to hold, place, and/or locate the nano-porous sections or portions 1408(1)-1408(6).

Because the nano-porous sections 1408(1)-1408(6) are made of material(s) having a geometrical network of interconnected nano-pores that do not have a critical dependence on the thickness of substrate 1402, an interconnect array structure may be constructed having greater total thickness—and thus—greater resistance to water permeability. Greater thickness can also allow for a more robust interconnect structure, which can provide increased ease in handling and forming (e.g., machining) to conform to different geometries such as the curvature of a target tissue or site.

With continued reference to FIG. 14, substrate 1402 can be made of a suitable material, e.g., dense non-porous aluminum oxide, while the nano-porous sections 1408(1)-1408(6) can be made from a suitable bio-compatible porous material. For example, the nano-porous sections 1408(1)-1408(6) can be made from suitably porous aluminum oxide. Other suitable materials may be used, e.g., hydroxyappatite, tri-calcium phosphate ceramic, sintered calcium phosphate (or other ceramics based on different calcium-phosphate ratios), nano-crystalline diamond, etc., and depending on the inclusion or absence of pores/voids these materials cab be used for either of the substrate and nano-porous sections 1408(1)-1408(6). For example, calcium phosphate powder may be applied (to a suitable base or substrate) and patterned to form the substrate with patterned channels, e.g., having width of 5 µm (which channels serve to receive the nano-porous sections) and then sintered (heated and fuzed) to a sufficient degree to remove porosity. Another amount of calcium phosphate may subsequently be applied to the substrate and sintered to a sufficient degree (preserving suitable porosity) to form the nano-porous sections 1408(1)-1408(6). For such embodiments, calcium and phosphate can be mixed in any of a number of suitable different stoichiometries to form different biocompatible ceramics.

While the claimed disclosure has been described in detail and with reference to specific embodiments thereof, it will be apparent to one of ordinary skill in the art that various changes and modifications can be made to the claimed disclosure without departing from the spirit and scope thereof. Thus, for example those skilled in the art will recognize, or be able to ascertain, using no more than routine experimentation, numerous equivalents to the specific substances and procedures described herein. Such equivalents are considered to be within the scope of this disclosure, and are covered by the following claims.

What is claimed is:

1. A microelectrode assembly for bio-stimulating and/or bio-sensing a target tissue comprising:
    a substrate having a first side and a second side, wherein the substrate includes a plurality of nano-porous portions, each extending through the substrate from the first side to the second side, and wherein the substrate comprises aluminum oxide; and
    an array of microelectrodes, each microelectrode including a nano-wire embedded within a nano-porous portion of the substrate and extending from a proximal end at the first side to a distal end at the second side, each nano-wire having a diameter less than 1 µm,
    wherein the substrate with the embedded nano-wires is fluid impermeable, and wherein the proximal ends are adapted to be connected to an electronic device and the distal ends are adapted to be disposed in a biological environment; and
    wherein the nano-wires include an alloy of about 88% platinum and about 12% iridium by molar fraction.

2. The assembly of claim 1, wherein the nano-porous portions include aluminum oxide.

3. The assembly of claim 1, wherein the nano-porous portions include calcium-phosphate.

4. The assembly of claim 3, wherein the calcium-phosphate includes tri-calcium phosphate.

5. The assembly of claim 1, wherein the plurality of nano-porous portions include hydroxyappatite.

6. The assembly of claim 1, wherein the plurality of nano-porous portions include nano-diamond.

* * * * *